United States Patent [19]

Vermillion

[11] Patent Number: 4,761,160

[45] Date of Patent: Aug. 2, 1988

[54] HUMAN MILK RETRIEVAL SYSTEM

[76] Inventor: Richard E. Vermillion, Rte. 1, Box 474 V, Chico, Calif. 95926

[21] Appl. No.: 49,158

[22] Filed: May 13, 1987

Related U.S. Application Data

[63] Continuation of Ser. No. 821,901, Jan. 23, 1986, abandoned.

[51] Int. Cl.$^4$ ............................................. A61M 1/06
[52] U.S. Cl. .................................................. 604/76
[58] Field of Search ............... 433/66, 92; 604/74–76; 84/399

[56] References Cited

U.S. PATENT DOCUMENTS

| | | | |
|---|---|---|---|
| 22,018 | 11/1858 | Davidson | 604/76 |
| 155,720 | 10/1874 | Gray et al. | 604/74 |
| 361,910 | 4/1887 | Tutton | 604/74 |
| 420,195 | 1/1890 | Graves et al. | 604/74 |
| 684,078 | 10/1901 | Martin | 604/74 |
| 2,208,089 | 7/1939 | Grolman | 604/74 |
| 2,419,795 | 4/1947 | Saunders | 604/74 |
| 3,339,444 | 9/1967 | Brooks | 84/399 |
| 3,738,363 | 6/1973 | Lunas et al. | 607/76 |
| 4,263,912 | 4/1981 | Adams | 128/281 |

FOREIGN PATENT DOCUMENTS

| | | | |
|---|---|---|---|
| 2208875 | 9/1973 | Fed. Rep. of Germany. | |
| 175154 | 4/1961 | Sweden | 84/399 |

Primary Examiner—C. Fred Rosenbaum
Assistant Examiner—J. L. Kruter

[57] ABSTRACT

The invention provides a system with hardware useful for artificial milk extraction from the human breast. Included is a conical breast cup placed over the mother's breast and a mouth piece on which the mother sucks. The sucking regulates a vacuum created in a baby bottle when air is removed through a tube in a vacuum cap on the bottle. The vacuum expresses milk from the nursing mother's breast similar to a suckling baby. The milk is drawn from the conical breast cup, along a milk tube, and into the baby bottle through a milk stem opening in the vacuum cap. During sucking, the vacuum created in the system holds the conical breast cup in position and allows the mother use of both hands. The filled baby bottle is then caped and the milk stored for future use.

1 Claim, 1 Drawing Sheet

HUMAN MILK RETRIEVAL SYSTEM

This is a continuation of application Ser. No. 06/821,901 filed 1/23/86 now abandoned.

BACKGROUND OF THE INVENTION

1. Field of the Invention

This invention relates to devices and systems for artifically releiving pressure from a nursing mother's breast and for retrieving a milk supply to be used when the mother is not available for breast feeding. The present invention is particularly directed towards human milk recovery devices designed for the nursing mother to use by herself.

2. Description of the Prior Art

The present invention is offered as an improvement over past art patented devices seen in the following patents:

Early human milk recovery methods and equipment includes the Gray and Gassin "Breast-Pumps" using a pliable bulb as a suction device. The patent is U.S. Pat. No. 155,720 and is dated Oct. 6, 1874. Then comes U.S. Pat. No. 361,910, dated Apr. 26, 1887, issued to A. B. Tutton, also a breast pump with a manually operated bulb pump. And the bulb pump action is seen again in U.S. Pat. No. 420,195, Graves and Hyer, Jan. 28, 1890. The pliable bulb pump is again seen in U.S. Pat. No. 684,078, W. H. Martin, issued Oct. 3, 1901.

Use of a replaceable bottle with measuring indicator marks is seen on July 16, 1940, in U.S. Pat. No. 2,208,089, granted to Grolman. The bulb pump is still in use on the device. A vacuum bottle is shown in Offenlegungsschrift No. 2208875, H. Marx, dated Sept. 6, 1973. The bulb action is again used to create the vacuum.

A suction tube wherein the mother regulates the pressure by drawing on a mouth piece is seen in U.S. Pat. No. 3,738,363, dated June 12, 1973, and granted to Lunas et al. A standard baby bottle can be used and the saliva trap is structured into the cap. And in a later patent issued to Adams, U.S. Pat. No. 4,263,912, dated Apr. 28, 1981, a return to the squeeze bulb is seen in an elaberlty structured device.

Patents seen as a part of the developing art of the human breast pump seem not to adequately cover the need for a simple, safe and sanitary device which will not cause discomfort to the user-mother. The present invention, therefor, is presented to fulfill that need.

SUMMARY OF THE INVENTION

To overcome those deficiencies noted in past art patented devices, in practicing my invention, I provide a pliable conical breast cup structured for user comfort. The apex of the conical breast cup is funnel shaped and a small extended end of the funnel is attached to a milk tube. A special cap fittable to standard nursing bottles has a double tube attachment on top. The milk tube from the conical breast cup is attached to one of the cap tube attachments. The other cap tube attachment is fitted with an air tube. The air tube runs to a mouth piece section which is equipped with a special cleanable sliva collector. The assemblage is arranged so the mother can suck on a mouth piece at one end of the mouth piece section. The suction creates a vacuum in the bottle and gently draws milk from the mother's breast on which she has placed the concial breast cup. The vacuum produced by the sucking holds the conical breast cup in place allowing the mother use of both hands. After drawing, the retrieved mother's milk may be cooled and rewarmed later for feeding at a convenient time.

Therefore, it is a principal object of this invention to provide a mother's milking system in which the mechanical suction device is eliminated and the suction pressure is determined by the individual user.

A further object of the invention is to provide a milking system for nursing mothers which can be used with standard baby bottles detachable from the system for storage of the expressed milk.

A still further object of the present invention is to provide a milking system for nursing mothers which is pain free and allows other use of both hands once the conical breast cup is in place and the system activated.

Another object of this invention is to provide a mother's milking system which allows immediate and gentle relief from breast enlargement without danger of broken suction action because of mechanical pump breakdown or extra appliances in the vacuum activating cap.

A further object of the invention is to provide a simple and practical milking system applicable to human needs which is highly portable so that today's mobile mother can easily take the packaged system with her for use at work or wherever she might be when the need arises.

Other objects and the many advantages of this invention will become better understood from a reading of the following specification and consideration the numbered parts described in conjunction with like numbered parts shown in the drawings.

Figure 1:
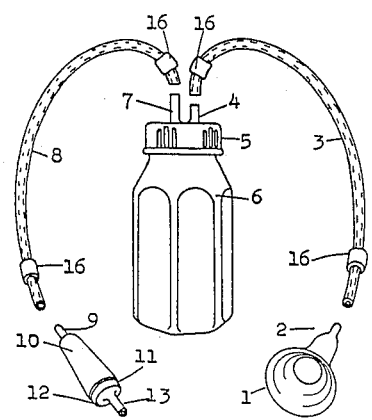
FIG. 1 shows the various parts of the human milk retrieval system ready for assembly.
Figure 2:
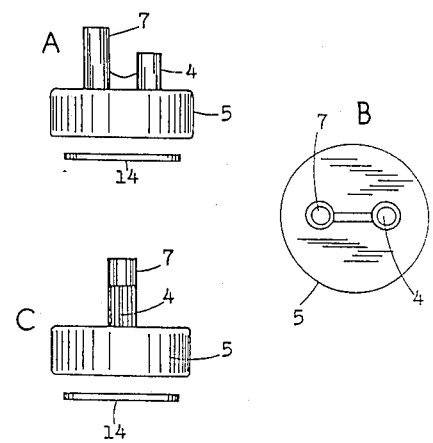
FIG. 2 is a drawing of the cap section in a side view at A with the sealer gasket shown below, the cap in a top plan view at B, and the cap in an end view at C with the sealer gasket below.
Figure 3:
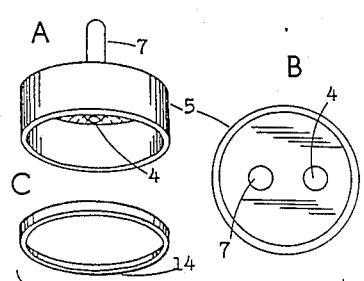
FIG. 3 illustrates the cap at A and the sealer gasket at C in a perspective drawing with the interior cap structure shown viewed from below at B.
Figure 4:
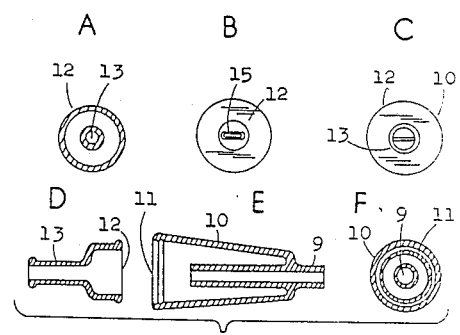
FIG. 4 is a sectional end view of the rounded mouth piece and mouth piece snap retainer base at A, an end view of the mouth piece retainer base with an elliptical mouth piece at B, and an end view of the mouth piece retainer base with a rounded mouth piece at C. A side sectional view of the rounded mouth piece and mouth piece snap retainer base is shown at D positioned for snap insertion into the saliva collector section shown at E in a sectional side view and in a sectional end view at F.
Figure 5:
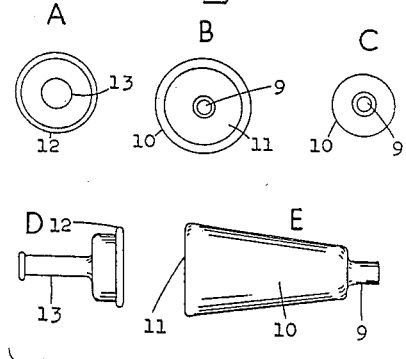
FIG. 5 shows the rounded mouth piece and mouth piece snap retainer base in an interior end view at A and shows the saliva collector section in an interior end view at B. An exterior end view of the rounded mouth piece and mouth piece snap retainer base is shown at C and in a side view at D, the mouth piece snap retainer base is shown positioned for snap insertion into the saliva collector section shown in a side view at E.
Figure 6:
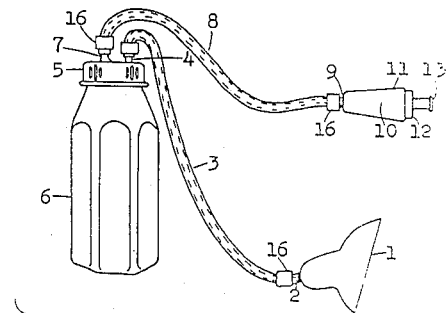
FIG. 6 illustrates the complete assemblage of the system parts.

DRAWING REFERENCE NUMERALS 1 conical breast cup
2 breast cup tube fitting 3 milk tube
4 milk collector stem
5 vacuum cap
6 baby bottle
7 air discharge stem
8 air tube
9 saliva collector section tube fitting
10 saliva collector section
11 collector snap-in receptacle
12 mouth piece snap retainer base
13 rounded mouth piece
14 vacuum sealer gasket
15 elliptical mouth piece
16 slide ring clamp

DESCRIPTION OF THE PREFERRED EMBODIMENT

Referring now to FIG. 1 in the drawings where the system parts are shown ready for assembly, the numbered parts illustrated include: conical breast cup 1 affixed with breast cup tube fitting 2 for attachment to milk tube 3 with the upper end of milk tube 3 positioned above milk collector stem 4 located in vacuum cap 5 in a central position. Vacuum cap 5 as shown is illustrated fastened to the top of baby bottle 6. Also in the top of vacuum cap 5 is a second protrusion, air discharge stem 7 with air tube 8 pictured above ready for installation. The lower end of air tube 8 fits saliva collector section tube fitting 9 affixed to saliva collector section 10. A collector snap-in receptacle 11 fastened to mouth piece snap retainer base 12 postions either rounded mouth piece 13 or elliptical mouth piece 15 for use. To assure a true vacuum seal, vacuum cap 5 is fitted with vacuum sealer gasket 14 at the mouth of baby bottle 6. Slip ring clamps 16 secure tubes 3 and 8 to breast cup tube fitting 2, to milk collector stem 4, to air discharge stem 7, and to saliva collector section tube fitting 9. If it is more comfortable for the user, rounded mouth piece 13 may be inserted into a short additional secondary tube 8 and the tube sucked on rather than the mouth piece. Vacuum developed in the system by the sucking holds conical breast cup 1 to the mother's breast allowing her use of both hands.

Although I have described the preferred embodiment of my human milk retrieval system with considerable detail in the specification, it is to be understood that certain modifications in the design and assemblage of parts may be made which do not depart from the scope of the invention as defined in the appended claims.

What I claim as my invention is:

1. A human milk retrieval system and elements thereof comprising:
   a breast cup;
   said breast cup conically formed, sized for human use, and structured of materials sufficiently pliable to accommodate various human breast configurations, there being an aperture positioned at the vertex of said conical form through said pliable materials affixed with an external opened protrusion providing a passageway therethrough and a tube attachment fitting thereto;
   a milk tube;
   said milk tube structured of pliable material, diametered sufficiently for the free passage of a liquid such as human milk therethrough and sized for attachment to said tube attachment fitting affixed to said breast cup, said milk tube being of a length adequate for attachment to a separately placed receptacle with the end thereof sized for fitting receptacle attachments;
   a vacuum cap;
   said vacuum cap being a lipped screw-type circular cap designed to fit a commercially available baby bottle with said baby bottle used as said receptacle for said human milk; said vacuum cap having two opened tubular external protrusions affixed as extended passageways for two apertures opened through the top covering of said vacuum cap with a shorter protrusion sized for the attachment of said milk tube thereto and a longer protrusion similarly sized as an air passage through said vacuum cap and for tubing attachment;
   an air tube;
   said air tube of pliable material, sized similarly to said milk tube, and diametered for attachment to said longer protrusion in said top of said vacuum cap with said air tube of sufficient length for attachment and use with said separately placed receptacle;
   a two piece pliable snap together saliva collector mouthpiece, said collector mouthpiece consisting of a mouthpiece section and a saliva collector section, said mouthpiece section having a circular distal base portion with an external lip ring means circumferentially about an opened and widened end thereof for snap attachment to the collector section proximal to said distal base portion of said mouth piece portion, which has a circular narrow tubular stem portion in fluid communication with said distal base portion; said saliva collector section of single unitary means composed of an external tubular collector portion having retainer edging means internally affixed at an opened widened end and a aperatured tubular longitudinally extending passageway at one end of which passes entirely within said collector portion the opposite end of which is of such dimensions that is is in fluid communication with said air tube, said tubular passageway of a lesser diameter than said external lip ring means is snapped into said retainer edging a saliva trap portion and a free air passage is formed by the connection of said saliva collector section and said mouthpiece section.

* * * * *